United States Patent [19]
Brosnahan et al.

[11] Patent Number: 5,620,445
[45] Date of Patent: Apr. 15, 1997

[54] MODULAR INTRAMEDULLARY NAIL

[76] Inventors: Robert Brosnahan, 2936 Waterleaf, Germantown, Tenn. 38138; Anthony James, 3605 Millie Dr., Bartlett, Tenn. 38135; Harry Lee, 7110 Pecan La., South Haven, Miss. 38617; Thomas A. Russell, 667 Arbor Edge Cir., Apt. 301, Memphis, Tenn. 38103

[21] Appl. No.: 275,806

[22] Filed: Jul. 15, 1994

[51] Int. Cl.⁶ .................................................. A61B 17/56
[52] U.S. Cl. ........................... 606/63; 606/62; 606/68
[58] Field of Search ........................... 606/62, 63, 64, 606/65, 66, 67, 68; 403/359; 623/23

[56] References Cited

U.S. PATENT DOCUMENTS

| | | |
|---|---|---|
| 3,846,846 | 11/1974 | Fischer . |
| 4,185,937 | 1/1980 | Anderson et al. .................. 403/383 |
| 4,622,959 | 11/1986 | Marcus . |
| 4,676,797 | 6/1987 | Anapliotis et al. .................. 623/23 |
| 4,776,330 | 10/1988 | Chapman et al. . |
| 4,805,607 | 2/1989 | Engelhardt et al. . |
| 4,827,917 | 5/1989 | Brumfield . |
| 4,858,601 | 8/1989 | Glisson . |
| 4,875,475 | 10/1989 | Comte et al. ........................ 606/64 |
| 4,940,467 | 7/1990 | Tronzo ................................ 606/66 |
| 4,995,883 | 2/1991 | Demane et al. .................... 623/23 |
| 5,047,033 | 9/1991 | Fallin ................................. 606/87 |
| 5,062,849 | 11/1991 | Schelhas ............................. 606/62 |
| 5,108,437 | 4/1992 | Kenna ................................. 623/23 |
| 5,108,452 | 4/1992 | Fallin ................................. 623/23 |
| 5,122,141 | 6/1992 | Simpson et al. .................... 606/64 |
| 5,169,259 | 12/1992 | Cornell, Jr. et al. .............. 403/361 |
| 5,352,227 | 10/1994 | O'Hara ............................... 606/63 |

FOREIGN PATENT DOCUMENTS 1031128  6/1953  France .

*Primary Examiner*—Michael Powell Buiz
*Assistant Examiner*—Mark S. Leonardo
*Attorney, Agent, or Firm*—Pravel, Hewitt, Kimball & Krieger

[57] ABSTRACT

A modular intramedullary nail has two or more modular components of varied sizes and designs, which are joined by a morse taper friction fit. Adjacent modular components are prevented from rotating relative to each other and can be properly aligned when assembled.

10 Claims, 8 Drawing Sheets

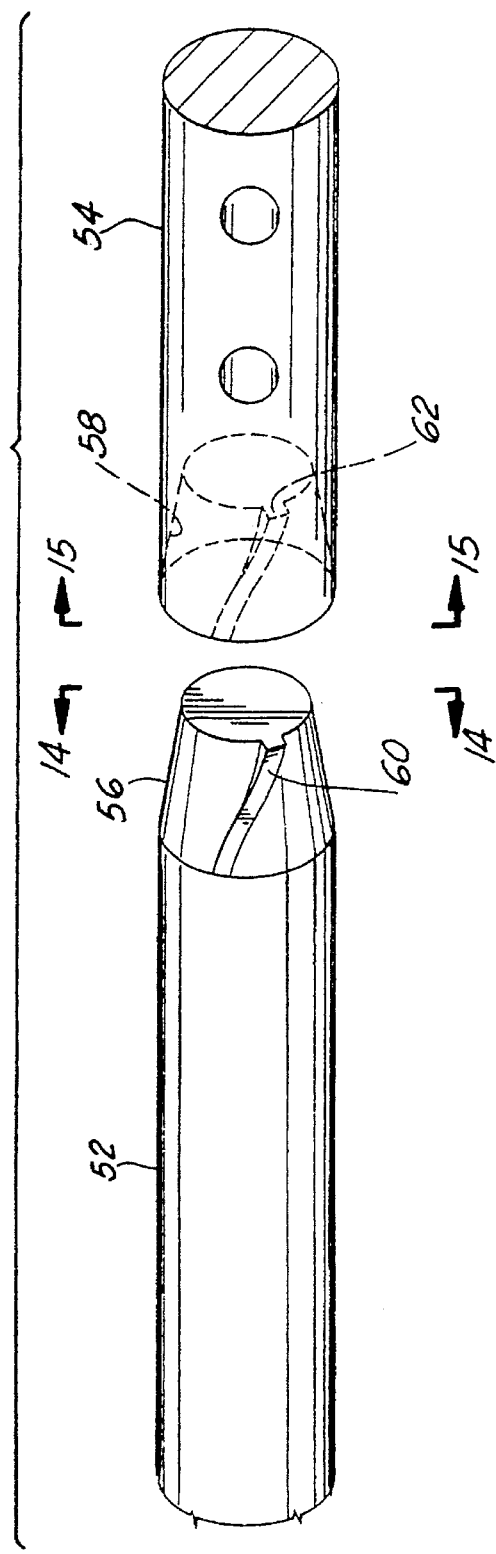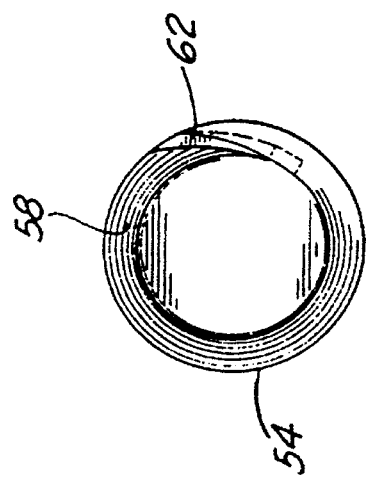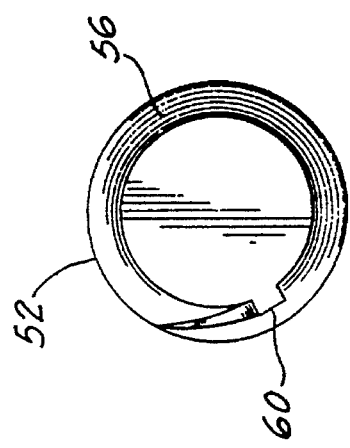
FIG. 13
FIG. 14
FIG. 15

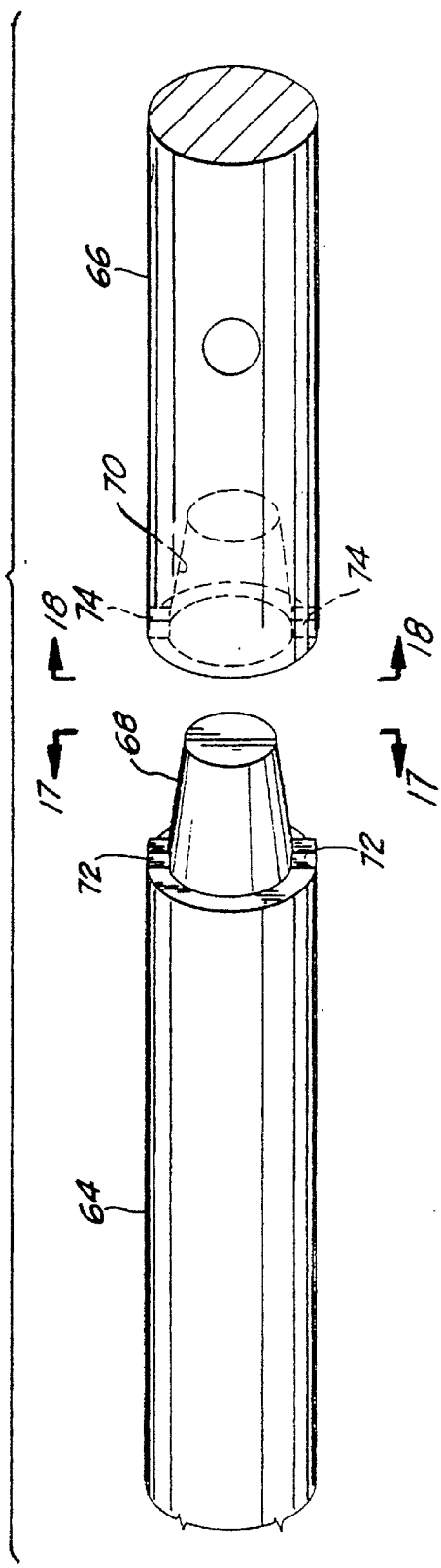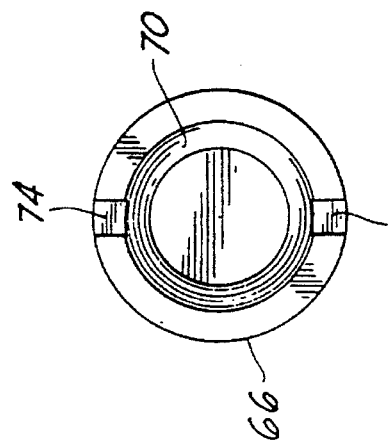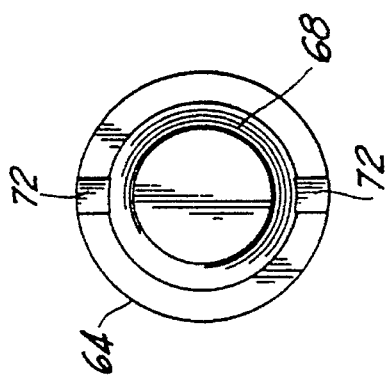

5,620,445

MODULAR INTRAMEDULLARY NAIL

SPECIFICATION

1. Field of the Invention

The present invention relates to an intramedullary nail system for the repair of long bone fractures, which has a modular design for enabling a surgeon to assemble a nail or related implant during surgery which most closely fits the patient's needs.

2. Background of the Invention

Intramedullary nails have become the preferred implant treatment in many long bone fracture cases. As the use of intramedullary nails has become more popular, the design of the implants has advanced so that there are particular designs for different types of fractures. Nails having a particular configuration are desirable for certain indications. Because of wide variation of the long bones in patients, the particular style of nail is preferably available in a range of lengths, diameters, and shapes. As a result, the surgeon must have at hand a large inventory of styles and sizes to accommodate the variety of indications. Examples of such styles include, but are not limited to femoral intramedullary nail, femoral reconstruction, intramedullary hip screw, and femur components of total hips.

One solution to this variation problem is to provide a modular nail system where a surgeon can select various component parts and assemble them to fit a particular patient's needs. Such a system is taught in U.S. Pat. No. 4,805,607 to Engelhardt et al. where a modular intramedullary nail system has elongated base nails and extension members of different lengths and diameters. The base nail is the primary structural component of the system and the extension member is designed to fit on the proximal end of a base nail. By selecting various combinations of base nails and extension members, nails of a desired length and diameter can be constructed. The component parts are locked together by a pair of snap lock springs formed on the proximal end of the base nail, which include engagement tongs with locking barbs at the trailing end which are radially depressed in order to engage a counterbore on the extension member. A screw is inserted through a hole in the modular components after the rod has been implanted for preventing the tongs from disengaging.

Another intramedullary nail is disclosed in the Simpson et al. U.S. Pat. No. 5,122,141, entitled "Modular Intramedullary Nail". In the Simpson patent, an intramedullary nail system and method for providing a capability of creating intramedullary nails of any desired length includes a combination of a small number of base nail members adapted to be joined to any one of a variety of hollow extension nail members. Any selected extension nail member may be axially connected to any selected base nail member in order to prevent axially separation of the members. Additionally, each extension nail members provided with transverse openings adapted to receive a bone screw to secure the intramedullary nail within the bone to be repaired. The extension nail member is infinitely rotationally adjustable about the axis of the base nail member in order to enable the fixation of the extension member with any desired degree of anteversion prior to final assembly of the base nail member with the extension nail member.

The Comte et al. U.S. Pat. No. 4,875,475 shows a device for treating a bone that includes an intramedullary nail adapted to be driven into a hollow bone. The proximal terminal nail segment includes an internal thread and a transversely penetrating longitudinal slot adapted to receive a screw to penetrate through the nail, and to be screw connected to the bone. A distal terminal nail section comprises two transversely throughgoing bores, each adapted to receive a screw to be screw connected with the bone.

The Chapman et al. U.S. Pat. No. 4,776,330 discloses a modular femoral implant system for use in the treatment of femoral disorders resulting from injury, disease, or congenital defects. The modular system includes at least three interconnected components, including an elongated epiphyseal-metaphyseal implant, an intramedullary rod, and an angled side plate having an elongated plate portion adapted to be secured to the outer cortical wall, and a hollow sleeve adapted to extend into the femur.

A French Patent No. 1,031,128 relates to a femoral nail of multiple sections.

The Fischer U.S. Pat. No. 3,846,846 discloses a ball-shaped portion to form part of the hip joint and a second portion that extends from the ball-shaped portion into the femur. The second portion is provided with a passage through which an elongated expander rod is extended which is also to be inserted into an opening in the femur and on the expanded rod is arranged a series of expansion elements in the form of a row which as the expander rod is moved longitudinally of the row are all expanded to anchor the prosthesis to the femur.

An adjustable compression bone screw is disclosed in the Glisson U.S. Pat. No. 4,858,601 that includes a shaft having first and second sections each with an external thread that may be rotated as a unit or independently. The screw includes means adapted to receive a first driving tool for driving the shaft as unit, and further adapted to receive a second driving tool for rotating the second section independently of the first section.

The Tronzo U.S. Pat. No. 4,940,467 discloses a variable length fixation device for insertion into a hole formed in two or more bone fragments and includes a barrel portion and a fastener element. The device is used for repair of the proximal portion of a patient's femur.

The Marcus U.S. Pat. No. 4,622,959, entitled "Multi Use Femoral Intramedullary Nail" discloses an intramedullary nail for use in fractures for the left or right femur and includes a body having a head, an intermediate portion, and a distal tip. Transverse openings are provided in the body near the distal tip and in the head for receiving locking screws. One opening in the head has its axis within the femoral neck and another opening has its axis generally transverse thereto. The nail head has a seat with a transverse locating slot for securing a screw insertion tool in a fixed angular position in which the screw guide on the tool is aligned with one of the screw receiving openings.

The Brumfield U.S. Pat. No. 4,827,917, entitled "Femoral Fracture Device," provides an apparatus for treating fractures of the femur that includes a screw and an intramedullary rod. The screw has a threaded portion and a smooth portion. The rod has a head, stem, and longitudinal bore. There is at least one pair of coaxial holes through the stem, transverse to the longitudinal axis of the rod, for receiving first anchoring means such as a nail, screw, or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw to permit the threaded portion of the screw, in use, to engage the femoral head and to allow sliding compression of a femoral neck or intertrochanteric fracture. An optional second anchoring means which will also allow sliding and compression and an optional set screw are also provided to adapt the fracture device to a variety of applications.

U.S. Pat. No. 4,995,883, issued to DeMane et al. and U.S. Pat. No. 5,108,452, issued to Thomas W. Fallin, both entitled "Modular Hip Prosthesis," disclose a modular hip prosthesis that can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion including an internal bore, and an attachment in the form of an elongated screw is provided for connection to the stem internal bore for securing the extension sleeve and the prosthesis body together, forming a compressive sealed connection therebetween. Pads can be attached to the transitional midsection of the prosthesis body for increasing the cross-sectional shape of the prosthesis at the transitional midsection. Removable collars can be added to the prosthesis to form a transverse load carrying interface with the upper end of the patient's femur. Frustro-conically shaped extension sleeves can be added to the prosthesis neck for extending the neck length.

U.S. Pat. No. 5,047,033, issued to Thomas W. Fallin, entitled "Mill And Guide Apparatus For Preparation Of A Hip Prosthesis," discloses a guide apparatus for preparing the femur of a patient with a rotary mill to receive a femoral hip prosthesis includes a V-shaped guide body having a lower end base portion adapted to extend into the intramedullary canal of the femur and an upper end portion comprised of at least two spaced apart struts so that the overall guide body had a configuration substantially the same as the prosthesis body sought to be implanted in the patient. The lower end of the guide body base provides one or more hemispherical receptacles for holding the hemispherical end portion of a spinning mill bit. A preferably removable transverse guide rail has connection pins at one end portion thereof for forming a connection with the upper end of the guide body at one of the struts, the arm having a curved surface that is adapted to guide the mill bit during preparation of the intramedullary canal of the patient's femur for receiving a hip prosthesis thereafter.

The inventors have determined it is advantageous to have a nail system with greater modularity than in a system such as shown in the Engelhardt patent, and one providing an easier and more secure method of attaching the components, which is assembled without utilizing a screw to hold the components together.

SUMMARY OF THE INVENTION

The present invention is directed to improved intramedullary nails providing a modular intramedullary nail system having preferably three modular components. Modular components include proximal and distal sections, and a central nail section, with each section constructed in a variety of sizes, diameters, and styles for fitting a wide range of anatomies and indications. The modular components of the present invention are quickly and easily assembled having joints of high mechanical and torsional integrity.

The modular components of the present invention preferably include a locking mechanism for connecting and locking together adjacent modular components which can quickly provide a positive locking fit that resists relative twisting or rotational movement between the components as well as translation. The locking mechanism also includes an facile alignment of components during the assembly process.

More specifically, assembly of the modular components of the present invention is achieved by one modular component having a bore with a tapered surface adapted to securely engage a cooperating tapered pin surface, with such engagement resulting in a secure connection which is resistant to rotational and translational forces. An example of a modified taper and bore providing such secure connection is a configuration known as a Morse taper. Resistance to relative rotational movement is achieved by providing a polygonal projection at the end of the taper. In the illustrated embodiment, the cooperating pin and bore are hexagonally shaped to achieve a snug fit.

In a preferred embodiment, the components are provided with an alignment mechanism to ensure the components are properly assembled. This is achieved, for example, by providing easily observed alignment indicia on the outer surfaces of the component parts, e.g., markings, indentations, tabs, flanges or keys on one component with corresponding indicia on the mating component. Asymmetric tabs, flanges or keys, and corresponding slots, may also be used to ensure the components are aligned in the proper configuration.

In an alternative embodiment, the taper or bore of one component may be adapted to accept more than one type of mated component, with each match corresponding to direct assembly of a specific implant design.

BRIEF DESCRIPTION OF THE DRAWINGS

In order to acquire a better understanding of the invention, reference may be had to a detailed description of exemplary embodiments set forth below, to be considered along with the appended drawings, in which:

FIG. 13 is a plan view, partially in section, of an alternative locking mechanism for the intramedullary nail system shown in FIGS. 1 and 2;

FIGS. 14 is an end view of the male portion of the alternative locking system shown as line 14—14 of FIG. 13;

FIGS. 15 is an end view of the female portion of the alternative locking system shown as line 15—15 of FIG. 13;

FIG. 16 is another alternative locking mechanism of the intramedullary nail system of the present invention;

FIGS. 17 is a end view of the alternative locking mechanism shown as line 17—17 of FIG. 16;

FIGS. 18 is a end view of the alternative locking mechanism shown as line 18—18 of FIG. 16;

DESCRIPTION OF THE EXEMPLARY EMBODIMENTS

Figure 1:
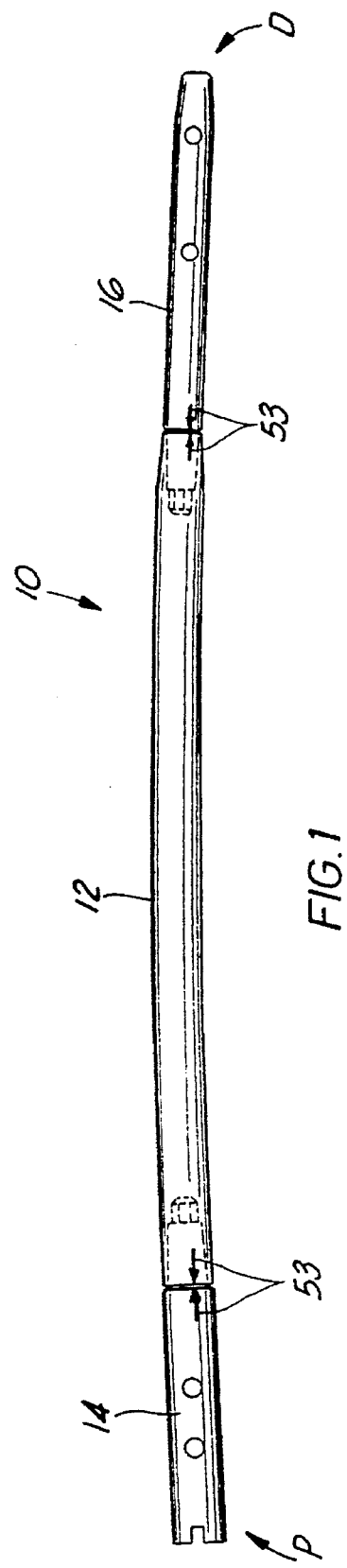
FIG. 1 is a plan view of a modular intramedullary designed in accordance with the present invention, in which the modular components are assembled.
Figure 2:
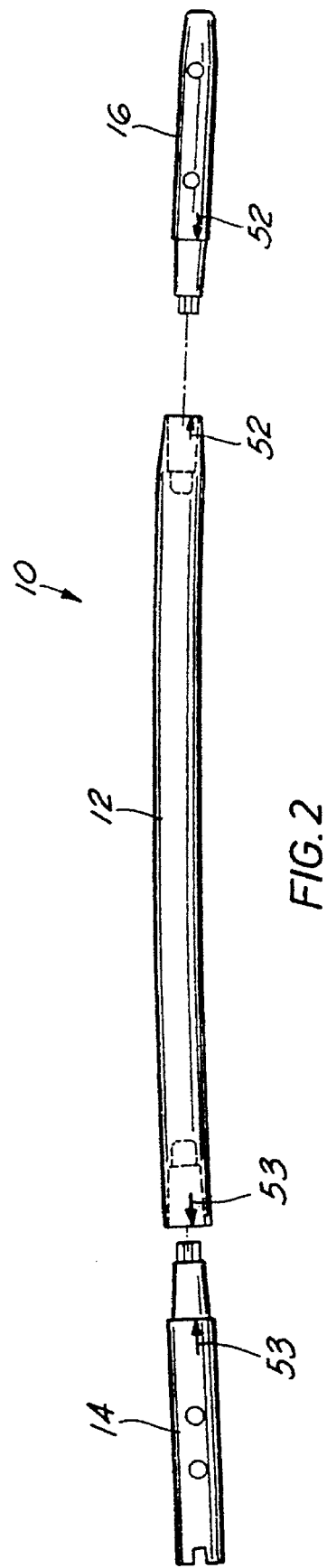
FIG. 2 is a plan view of view of the modular system shown in FIG. 1, with the distal and proximal sections separated from the central section.

Referring to FIGS. 1 and 2, one exemplary embodiment of the modular intramedullary nail system of the present invention is shown. The term "modularity" for the system of the present invention is used to describe the various sections which are used to make up an assembled nail 10 as shown in FIG. 1. The nail 10 is formed of two or more, and preferably three discreet sections, a central section 12, a proximal section 14 to form a proximal end P and a distal section 16 to form a distal end D. When assembled as shown in FIG. 1, the sections form a complete intramedullary nail which in accordance with known surgical procedures can be inserted into a long bone of a patient in order to stabilize a fracture.

FIG. 2 shows the system of FIG. 1 with the three components in a disassembled state. As may be appreciated, each of the components is only one of a number of different sizes and styles available to the physician so that the system shown in FIGS. 1 and 2 represent the desired or appropriate system as finally determined by the surgeon.

As shown in FIG. 2, the component sections are separate elements which are manufactured independently and need to be assembled in order to form the operative nail. The modularity of this product is advantageous since it permits a surgeon to select the appropriate components for a particular patient from a variety of sizes, shapes and styles, and assemble those components in order to provide a nail having the proper characteristics for the specific indications.

The nail 10 of the present invention has a locking mechanism between adjacent components which is designed so that the pieces may easily be fitted together and locked to each other such that they will resist separation and rotational movement relative to each other when they are subjected to stresses after implantation.

Figure 6:
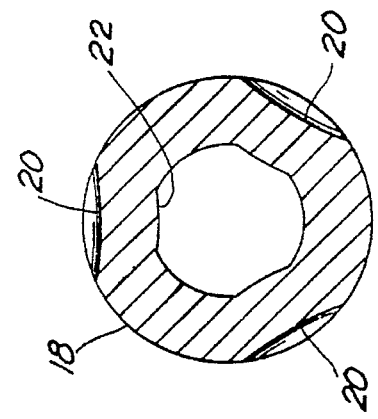
FIG. 6 is a section view looking through a section line 6—6 of FIG. 3.

As shown in greater detail in FIGS. 3–6, the central section 12 has an elongated portion 18 with flutes 20 on its outer surface and a hollow opening 22 which is generally similar in shape to the outer surface (see FIG. 6).

Figure 3:
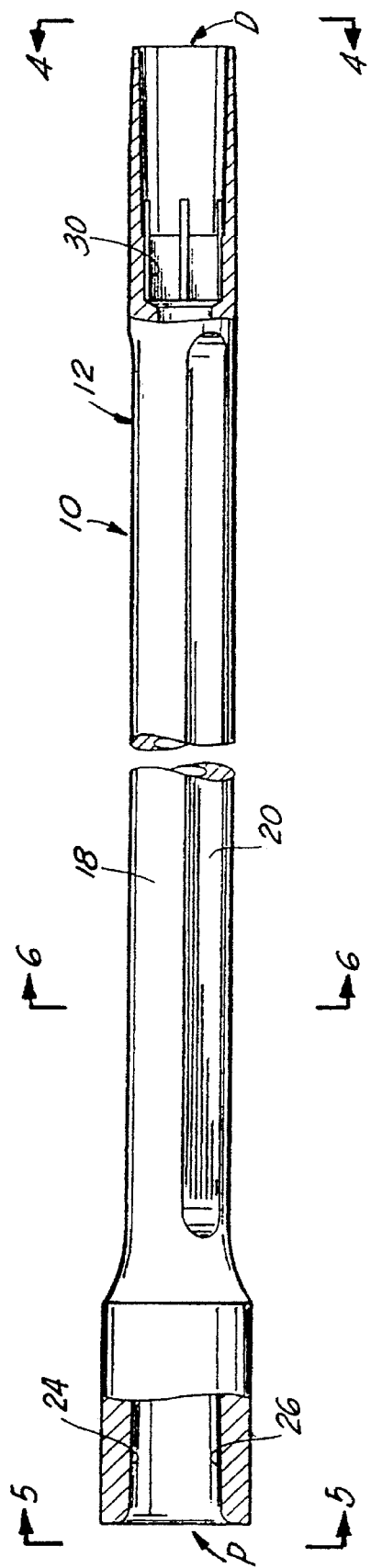
FIG. 3 is a plan view, partially in section, of the central section of the modular system showing in particular the female sockets at both ends.
Figure 5:
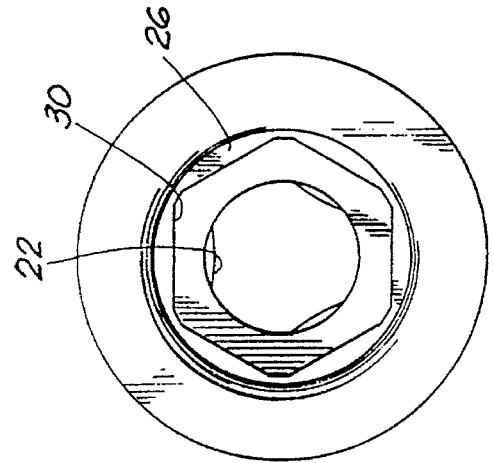
FIG. 5 is a second end view of the central section shown in FIG. 3.
Figure 4:
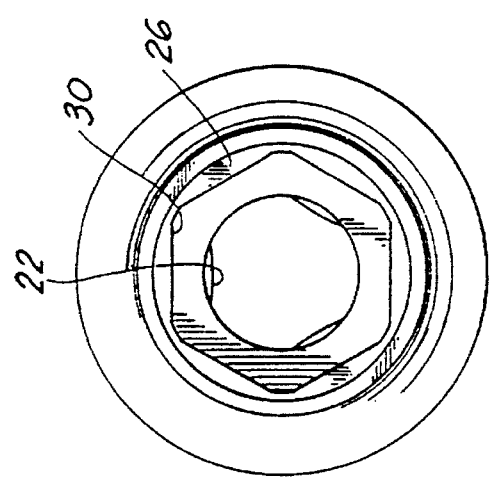
FIG. 4 is an end view of the central section shown as line 4—4 in FIG. 3.

A socket or female connection 24 is formed in both ends of the central section 12 as shown in FIGS. 3–5. The only difference between the two ends illustrated is that the distal end D has a smaller diameter than the proximal end P. The configuration of both sockets or female portions 24 of the locking mechanisms are similar. They include a tapered inner wall 26 which is conical in shape and decreases in diameter from the outer open portion of the socket inwardly. The tapered wall 26 is adapted to mate with a tapered male connection section 28 formed on proximal section 14 or distal section 16 (see FIGS. 7, 10, 11, and 12). The tapered surfaces 26, 28 are complementary and taper at an equal angle so that the two surfaces form a self-locking fit such as is commonly known as a Morse taper. This type of fitting is characterized by forming a tight friction-fit upon impact.

The proximal and distal sections 14, 16 may be locked into sockets 24 by simply inserting them as shown generally in FIG. 1 and then impacting the outer end of the sections in order to lock the Morse taper. In the preferred embodiment, an impact driver may be used by the surgeon to provide the impact. Such an impact driver is a commercially available product which carries a tooled end portion having, for example, a commercial screw driver or wedge tip (not shown). One driver which has been found appropriate for medical products is supplied by the Starrett Company, which impacts as much as 300 pounds of load when it is used.

Although the modular components are illustrated as having female tapers on the central section and cooperating male tapers on the proximal and distal sections, it is understood that any combination of cooperating male and female tapers may be used to achieve the desired connections.

For some indications, e.g., those requiring a large diameter nail, the inside diameter of the nail cannula may be larger than the diameter of the taper. For example, a "bottle bore" configuration may be used, where the ends of nail segment are compressively swagged to a smaller diameter, that is, the outer surface of the nail segment is simultaneously and uniformly pinched so as to form a tapered diameter required for fitting together the modular components.

Figure 7:
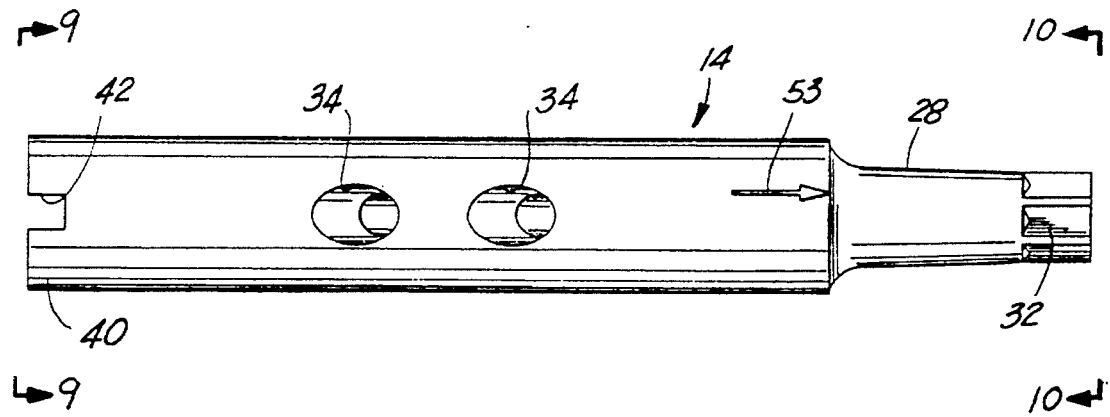
FIG. 7 is a plan view of the proximal end of the modular system shown in FIGS. 1 and 2.

In order to hold the adjacent components together and to prevent them from twisting relative to each other after implantation in a human bone, the socket or female receptacle is formed with a polygonal, e.g., hexagonal opening 30 on the inner end of the tapered surface 26, which is sized and shaped to mate with a hexagonal male projection 32 formed on the outer end of the male taper 28 (see FIG. 7). The cooperating polygonal, e.g., hexagonal female and male sections 30, 32 are closely machined so that little if any relative twisting movement takes place between the adjacent modular components after the nail 10 is implanted. Obviously, other shapes may be used for these mating components in order to prevent this twisting action from taking place. The cooperating angular mating components may be used to align adjacent components in one or more preferred orientations, simply by rotating the components relative to each other.

Figure 25:
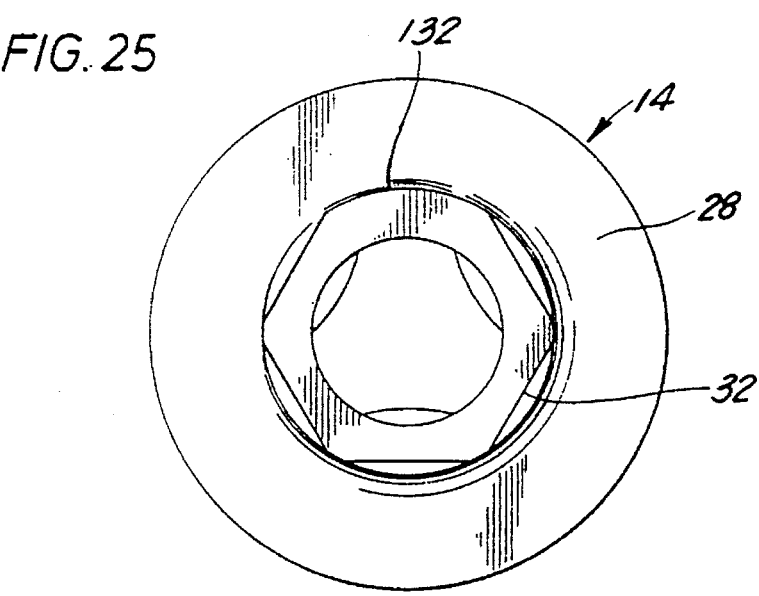
FIGS. 25–26 are schematic fragmentary views of the preferred embodiment of the apparatus of the present invention illustrating the mating angular socket and projection portions thereof.
Figure 26:
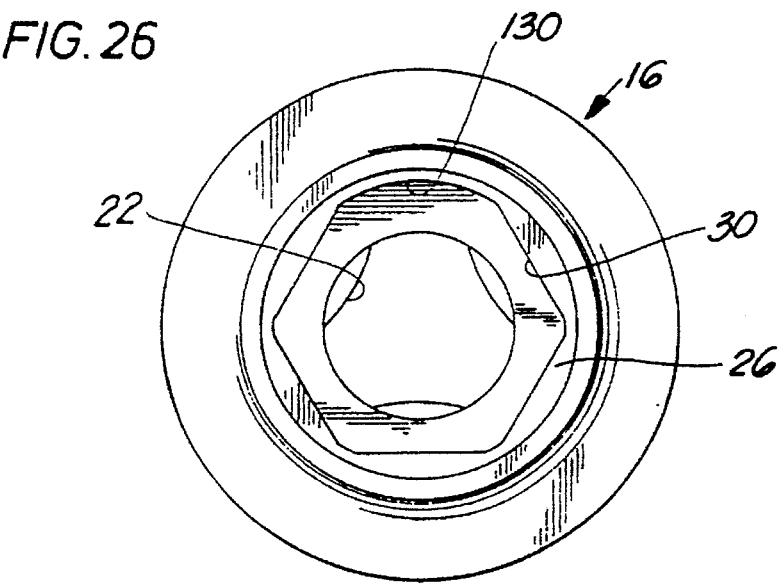

In a preferred embodiment, the mating angular projection and socket are asymmetrical. As illustrated in FIGS. 25 and 26, the hexagonal projection 32 and its corresponding socket 30 may be rounded at one facet 130, 132. Such asymmetry permits the cooperating ends to fit together only in a desired orientation and prevents incorrect alignment of component parts.

Figure 8:
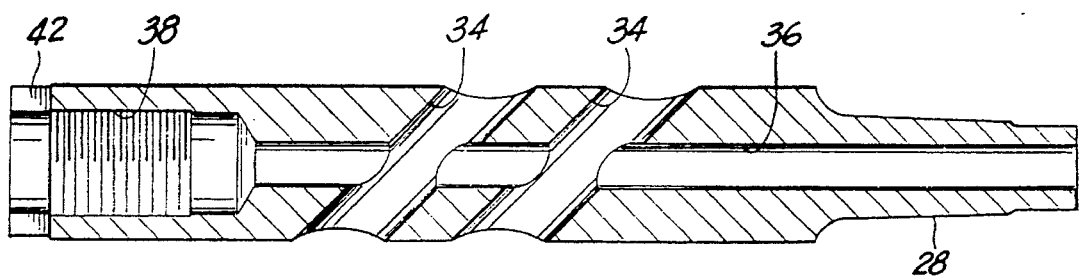
FIG. 8 is a sectional view of the proximal end shown in FIG. 7, rotated 90° from the view shown in FIG. 7.
Figure 9:
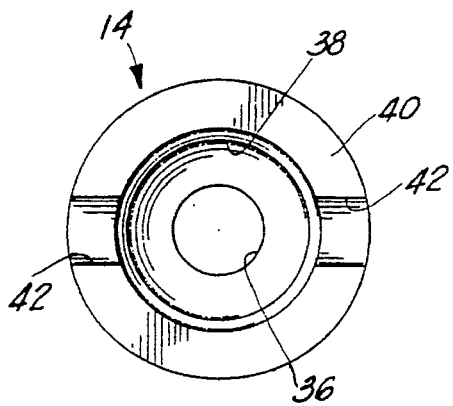
FIG. 9 is an end view of the proximal end shown as line 9—9 in FIGS. 7 and 8.
Figure 10:
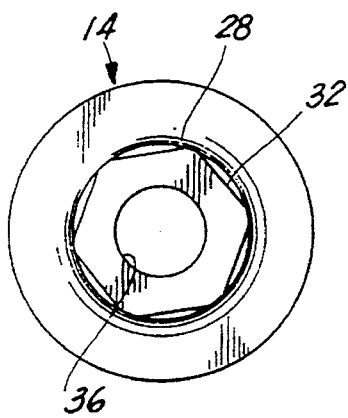
FIG. 10 is a second end view of the proximal end shown as line 10—10 in FIGS. 7 and 8.

As shown in FIG. 7, the proximal end is provided with a pair of openings 34 in order to accommodate screws for holding the nail 10 relative to the bone in which it is implanted. As shown in FIG. 8, the proximal section 14 includes a hollow center opening 36 and a threaded female receptacle 38 for receiving a tool (not shown) for removing the nail if necessary. A notch 42 is formed at the outer end of the distal section 14 which cooperates with a tool (not shown) for inserting the nail in the bone of the patient.

Figure 11:
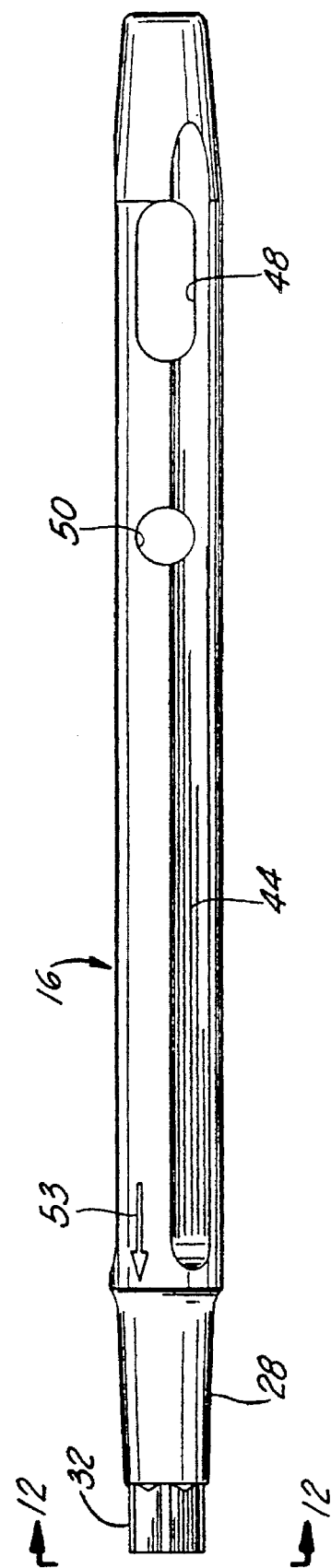
FIG. 11 is a plan view of the distal section of the modular system shown in FIGS. 1 and 2.
Figure 12:
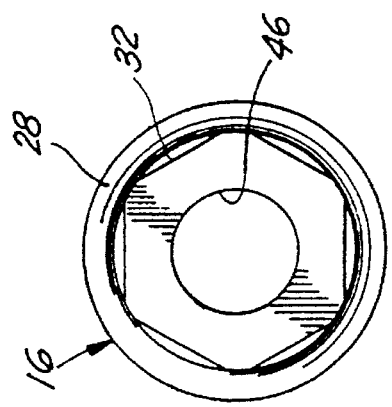
FIG. 12 is an end view of the distal section shown as line 12—12 in FIG. 11.
Figure 19:
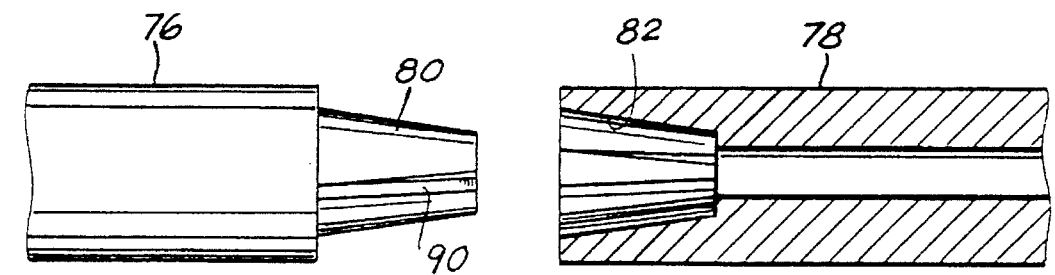
FIG. 19 is a plan view partially in section, of another alternative locking mechanism in accordance with the present invention.
Figure 20:
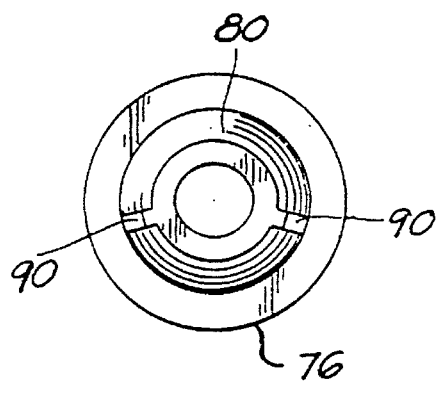
FIGS. 20–22 are end views of three male components for the alternative embodiment shown in FIG. 19.
Figure 21:
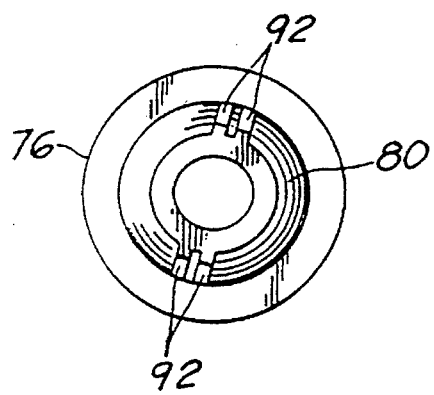
Figure 22:
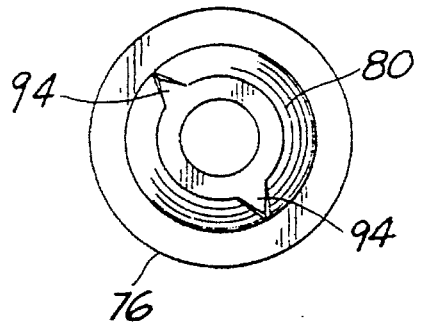
Figure 23:
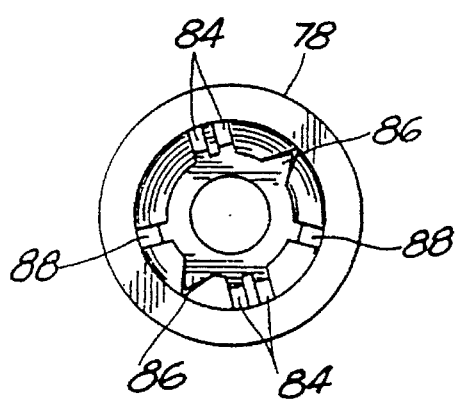
FIG. 23 is an end view of the female component for the alternate embodiment shown in FIG. 19.

A preferred embodiment of the distal section 16 is shown in FIGS. 11 and 12 where, in addition to the tapered surface 28 and hexagonal projection 32, the outer surface includes elongated flutes 44 and an opening 46 which extends along the axis of the proximal section 16. A pair of openings 48, 50 are provided to accommodate anchoring screws.

As shown in FIGS. 1 and 2, a pair of alignment arrows 53 are formed on the outer surface of the adjacent components in order to indicate to the surgeon the proper alignment of the sections relative to each other. These arrows may be scratched, etched or otherwise marked on the outer surface of the various sections. Any type of indicia which provide for a visual or mechanical indication of the proper orientation between the adjacent sections may be used.

Another way to insure proper alignment is by using a design such as that shown in the embodiment of FIGS. 13–15 where adjacent nail sections 52, 54 have cooperating male and female sections in the form of a tapered outer surface 56 and a tapered inner surface 58 for providing a Morse taper fit as described above. However, as shown best in FIGS. 14 and 15, the male tapered surface 56 has a projection 60 formed on its outer surface which is sized and shaped to fit into a slot 62 which extends from the surface of the tapered receptacle 58. The cooperation between the projection 60 and slot 62 provides resistance against any relative twisting between the adjacent components 52, 54 as well as to insure that the components are properly aligned when they are assembled.

Another embodiment of the locking mechanism is shown in FIGS. 16–18 where adjacent components 64, 66 have cooperating male and female tapers 68, 70 which lock together as discussed above. Instead of a projection 60 as shown in FIG. 13, a pair of flanges 72 are formed adjacent to the male taper 68, which fit into a pair of slots 74 formed adjacent to the female taper 70.

Another alternative locking mechanism is shown in FIGS. 19–23 where adjacent sections 76, 78 are provided with cooperating male and female tapers 80, 82. The female taper 82 has a series of slots 84, 86, 88 shown in FIG. 23, which cooperate with various shapes of projections formed on the male taper 80 shown in FIGS. 20–22. For example, the projections 90 shown in FIG. 20 mate with the slots 88 shown in FIG. 23, the projections 92 in FIG. 21 with the slots 84 in FIG. 23 and the projections 94 in FIG. 22 with the slots 86 in FIG. 23. Each of the sets of projections 90, 92 and 94 are different shapes and configurations so that only the projections designed to fit in a cooperating set of slots will allow insertion in those slots. This insures proper alignment between each individual component section 76 in the proper orientation without any mismatching. The use of the slots and projections also prevent relative twisting movement between the components after they are implanted in the human body.

Figure 24:
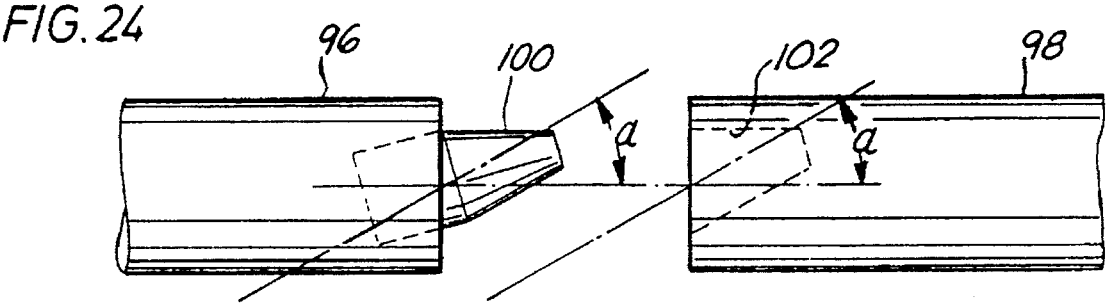
FIG. 24 is a plan view of another alternative locking mechanism.

Another embodiment for insuring rotational stability between adjacent components as shown in FIG. 24 where the adjacent components 96, 98 have cooperating male and female tapered surfaces 100, 102 which are offset at an angle α relative to the longitudinal axis of the components 96, 98, so that proper alignment and resistance against relative twisting movement are provided. This angled taper embodiment may also be employed to connect modular components resulting in the axis of either or both of the proximal or distal sections 14, 16 being oriented at an angle relative to the axis of the central section 12.

The foregoing description should be considered exemplary of the invention and not restrictive. It should also be understood that improvements and modifications can be made to the invention without departing from the spirit and scope of the invention as defined in the appended claims.

We claim:

1. A modular intramedullary nail, comprising:

a) a proximal nail component;

b) a distal nail component;

c) a central nail component having proximal and distal end portions that are respectively connected during use to the proximal and distal nail components to define therewith upon assembly a modular intramedullary nail unit having a generally smooth continuous outer surface of generally uniform outer diameter and that is free of sharp curves, enabling the assembled nail unit to be surgically inserted into a patient's intramedullary canal;

d) connecting portions for securing the proximal and distal nail components to the respective proximal and distal end portions of the central nail component, the connecting portions including corresponding male and female conical connector sections, the conical connector sections being tapered at about the same angle so they can be fitted and secured together;

e) the connecting portions including self orienting interlocking portions on the proximal and distal nail components adjacent the conical sections for resisting relative rotational movement between the components;

f) said interlocking portions comprising at least in part a plurality of flat surfaces carried by the male conical connector section and a correspondingly shaped plurality of flat surfaces carried by the female connector section; and wherein the central nail component is much larger than either of the proximal or distal nail components.

2. The modular nail of claim 1, further including alignment means associated with the connecting means for assuring proper alignment between the components.

3. The modular nail of claim 2, wherein the proximal and distal nail components are elongated hollow members.

4. The modular nail of claim 1, wherein the connecting portions have male and female connector sections that are generally frusto-conical in shape.

5. The modular nail of claim 1, further comprising alignment means for aligning adjacent nail sections that includes indicia formed on the outer surface of adjacent nail components.

6. The modular nail of claim 1, wherein the self-orienting interlocking portions includes at least one set of cooperating shaped projections and slots on the male and female connector sections.

7. The modular nail of claim 6, wherein at least one shaped projection and slot are formed on the conical connector sections.

8. The modular nail of claim 6, wherein at least one shaped projection and slot are formed adjacent to the conical connector sections.

9. The modular nail of claim 1, wherein the self-orienting locking portions include a shaped projection on the male connector section and a corresponding shaped socket on the female connector section, the projection and socket each being shaped to prevent relative rotational movement when they are assembled.

10. The modular nail of claim 9, wherein the shaped projection and socket are hexagonal.

* * * * *